(12) United States Patent
Kang

(10) Patent No.: US 9,669,050 B2
(45) Date of Patent: Jun. 6, 2017

(54) COMPOSITION FOR PREVENTION OR TREATMENT OF HYPERLIPIDEMIA, FATTY LIVER OR OBESITY

(75) Inventor: Seung Woo Kang, Seoul (KR)

(73) Assignee: BENEBIOSIS CO., LTD., Seoul (KR)

( * ) Notice: Subject to any disclaimer, the term of this patent is extended or adjusted under 35 U.S.C. 154(b) by 109 days.

(21) Appl. No.: 13/056,805

(22) PCT Filed: Jul. 31, 2009

(86) PCT No.: PCT/KR2009/004301
§ 371 (c)(1),
(2), (4) Date: Jan. 31, 2011

(87) PCT Pub. No.: WO2010/013978
PCT Pub. Date: Feb. 4, 2010

(65) Prior Publication Data
US 2011/0135717 A1    Jun. 9, 2011

(30) Foreign Application Priority Data

Aug. 1, 2008  (KR) .................. 10-2008-0075659
Apr. 14, 2009  (KR) .................. 10-2009-0032463

(51) Int. Cl.
| | | |
|---|---|---|
| *A61K 31/702* | (2006.01) | |
| *C07H 3/06* | (2006.01) | |
| *A61K 31/715* | (2006.01) | |
| *A61K 31/7016* | (2006.01) | |
| *A23L 33/10* | (2016.01) | |

(52) U.S. Cl.
CPC ............ *A61K 31/715* (2013.01); *A23L 33/10* (2016.08); *A61K 31/702* (2013.01); *A61K 31/7016* (2013.01); *C07H 3/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,925,680 A | 5/1990 | Schweikhardt et al. |
| 5,118,516 A | 6/1992 | Shimatani et al. |
| 6,706,497 B2 | 3/2004 | Pelletier et al. |
| 8,440,178 B2 * | 5/2013 | Darimont et al. ........... 424/93.3 |
| 2004/0265462 A1 | 12/2004 | Carlson |
| 2006/0062859 A1 | 3/2006 | Blum et al. |

OTHER PUBLICATIONS

"Heart and blood vessel disorders", Merck Manual Online Edition, [retrieved on Jan. 30, 2013]. Retrieved from the Internet http://www.merckmanuals.com/home/. Revision Jan. 2008., 11 pages.*
Lara-Villoslada et al., Clinical Nutrition, 2006, 25, 477-488.*
Merriam-Webster's Collegiate Dictionary, Tenth Edition, copyright 1998, Merriam-Webster, Incorporated, pp. 924 and 935.*
Karmiris et al., "Circulating Levels of Leptin, Adiponectin, Resistin, and Ghrelin in Inflammatory Bowel Disease" Inflammatory Bowel Disease (2006) vol. 12 No. 2 pp. 100-105.*
Blackburn, George, "Effectof Degree of Weight Loss on Health Benefits" Obesity Research (1995) vol. 3 suppl. 2, pp. 211s-216s.*
International Search Report from International Application No. PCT/KR2009/004301, dated Mar. 9, 2010 (date of completion of search) and Mar. 10, 2010 (date of mailing of report).

* cited by examiner

*Primary Examiner* — Eric Olson
(74) *Attorney, Agent, or Firm* — Harness, Dickey & Pierce, P.L.C.

(57) ABSTRACT

Disclosed is a composition for prophylaxis or treatment of hyperlipidemia, fatty liver, cardiovascular disease, or obesity including a compound represented by General Formula I as an effective ingredient: General Formula I S-$(MS)_p$-$(MS)_q$ wherein S represents sialic acid, and $(MS)_p$ and $(MS)_q$ independently represent a monosaccharide residue.

19 Claims, 12 Drawing Sheets

Time (days)

HD

HD + SL (1 mg/kg)

COMPOSITION FOR PREVENTION OR TREATMENT OF HYPERLIPIDEMIA, FATTY LIVER OR OBESITY

CROSS-REFERENCE TO RELATED APPLICATIONS

This application is the U.S. national stage filing under 35 U.S.C. §371 of international application PCT/KR2009/004301, filed Jul. 31, 2009, which claims benefit of Korean Patent Applications 10-2008-0075659, filed Aug. 1, 2008, and 10-2009-0032463, filed Apr. 14, 2009.

TECHNICAL FIELD

The present invention relates to a composition for prophylaxis or treatment of hyperlipidemia, fatty liver, cardiovascular disease or obesity.

BACKGROUND ART

Obesity is a common disease caused by multiple factors and is accompanied by many complications such as hyperlipidemia, fatty liver, arteriosclerosis, cardiovascular disease, hypertension, diabetes, or the like. Recently, obesity is becoming a severe social problem as the diet is westernized. As if to reflect this, the World Health Organization (WHO) defined obesity as one of chronic diseases in 1997.

Obesity is a direct or indirect cause of many adult diseases, including diabetes, hypertension, hyperlipidemia, cholelithiasis, etc. It is a severe problem in that it can be fatal physically or mentally and may cause tremendous sociological or economic losses.

The WHO has warned that the current overweight or obese populations reaching 1 billion will increase by 50% to 1.5 billion in 2015 and will be a major concern of health (Sep. 22, 2005). Overweight and obesity are major risk factors of cardiovascular disease, the number one cause of death in the world. Each year, more than 170 million people die of cardiovascular disease, about 80% among them in the United States and other developed countries. The WHO analyzes that the obesity, which has been considered only as the developed countries' problem, is spreading worldwide with increased fat, salt or sugar in foods, lack of physical activity, development in transportation, or the like. Actually, the countries where 75% or more of the women aged 30 or more are overweight include the United States, Egypt, Mexico, South Africa and Turkey, and the countries where 75% or more of the men aged 30 or more are overweight include the United Kingdom, Argentina, Germany, Greece, Kuwait and New Zeeland.

Also, reporting that the increase of the overweight and obese population is really surprising, the WHO predicts that the rapid increase of the overweight or obese population, particularly in underdeveloped countries, will be a major cause of increased chronic diseases within 10-20 years if no measure is taken.

The main treatment for obesity consists of dieting, physical exercise and drug therapy. According to clinical results, those who received drug therapy along with dieting and physical exercise experienced about 2 times more body weight loss in two years than those who underwent dieting and physical exercise only. Further, they also showed marked improvement in blood pressure, blood sugar and cholesterol.

Accordingly, interest in drug therapy and development of obesity therapeutic agent is increasing.

Anti-obesity drugs inhibit obesity by suppressing appetite, promoting metabolism or inhibiting absorption of specific nutrients in foods. As the structure and function of melanocortins and anorectic peptides known to have appetite suppressing effect, such as bombesin, are known, the development of anti-obesity drug is facing an important turning point.

At present, typical anti-obesity medications are sibutramine (brand name: Reductil, Meridia in USA) and orlistat (brand name: Xenical, Alli). Sibutramine inhibits reuptake of serotonin and noradrenaline, neurotransmitters involved in regulation of appetite, therefore decreasing appetite. However, frequently encountered side effects are dry mouth, paradoxically increased appetite, nausea, strange taste in the mouth, upset stomach, constipation, trouble sleeping, dizziness, drowsiness, menstrual cramps/pain, headache, joint/muscle pain, or the like. Sibutramine can substantially increase blood pressure and pulse in some patients. Therefore regular monitoring needs to be performed. The following side effects are infrequent but serious and require immediate medical attention: cardiac arrhythmias, paresthesia, mental/mood changes, or the like. In addition, careful monitoring is needed as the safety issue of sudden death, heart failure, kidney failure, gastrointestinal disorder, etc. is raised. Furthermore, because such a general appetite suppressant affects the metabolism of proteins and carbohydrates, as well as fats, selective weight loss is impossible. Orlistat treats obesity by reducing intestinal fat absorption. It is marketed as Xenical, but has side effects such as steatorrhea, intestinal gas production, abdominal swelling, or the like, and has limited effect on those who go on a low-fat diet.

Other medications for suppressing appetite are developed, but most of them are associated with mental side effects.

Throughout this specification, a number of literatures and patent documents are referenced and cited. The disclosure of the cited literatures and patent documents are incorporated herein to more clearly explain the background art and the present invention.

DISCLOSURE

The inventors of the present invention have made efforts to develop a substance capable of preventing or treating hyperlipidemia, fatty liver, cardiovascular disease or obesity in order to overcome the side effects of existing medications and to avoid the chronic diseases.

The inventors of the present invention have made efforts to develop a substance capable of reducing body weight or reducing blood lipid level. As a result, they have confirmed that sialyloligosaccharide induces body weight loss, HDL-cholesterol increase, LDL-cholesterol decrease and leptin decrease in a high-fat diet obesity model, and thus is able to prevent or treat hyperlipidemia, fatty liver, cardiovascular disease or obesity, and have completed the present invention.

Accordingly, an object of the present invention is to provide a composition for prophylaxis or treatment of hyperlipidemia, fatty liver, cardiovascular disease or obesity.

Another object of the present invention is to provide a method for prophylaxis or treatment of hyperlipidemia, fatty liver, cardiovascular disease or obesity.

DESCRIPTION OF DRAWINGS

The above and other objects, features and advantages of the present invention will become apparent from the following description of preferred embodiments given in conjunction with the accompanying drawings, in which.

BEST MODE

Figure 1A:
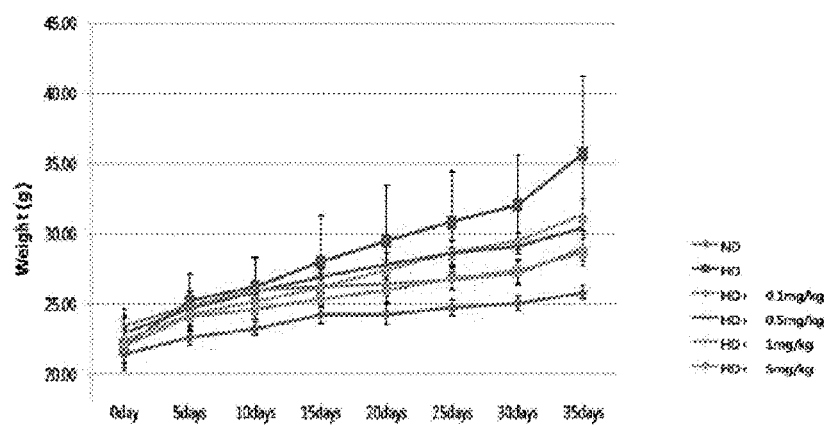
FIG. 1a is a graph showing the body weight change of high-fat diet C56BL/6 male mice [ND, HD and HD+3'-SL represent a normal diet group (normal group), a high-fat (60% fat) diet group (control group) and a high-fat diet group treated with 3'-sialyllactose (3'-SL), respectively.]

Hereinafter, the embodiments of the present invention will be described in detail with reference to accompanying drawings.

Unless otherwise defined, all terms (including technical and scientific terms) have the same meaning as commonly understood by one of ordinary skill in the art. In the following description and drawings, details of well-known features and techniques may be omitted to avoid unnecessarily obscuring the present invention.

In an embodiment, the present invention provides a composition for prophylaxis or treatment of hyperlipidemia, fatty liver, cardiovascular disease or obesity comprising a compound represented by General Formula I as an effective ingredient:

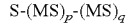
General Formula I wherein S represents sialic acid, and $(MS)_p$ and $(MS)_q$ independently represent a monosaccharide residue.

In another embodiment, the present invention provides a method for prophylaxis or treatment of hyperlipidemia, fatty liver, cardiovascular disease or obesity comprising administering a composition comprising a compound represented by General Formula I as an effective ingredient to a subject:

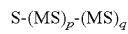
General Formula I wherein S represents sialic acid, and $(MS)_p$ and $(MS)_q$ independently represent a monosaccharide residue.

The inventors of the present invention have made efforts to develop a substance that reduces body weight or blood lipid level. As a result, they have confirmed that sialyloligosaccharide induces body weight loss, HDL-cholesterol increase, LDL-cholesterol decrease and leptin decrease in a high-fat diet obesity model, and thus is able to prevent or treat hyperlipidemia, fatty liver, cardiovascular disease or obesity.

In the present invention, the effective ingredient is a compound represented by General Formula I. In General Formula I, S represents sialic acid. Sialic acid may be bound to $MS_p$ in various manners. It may be bound to the monosaccharide compound $(MS)_p$ via α-2,3 or α-2,6 linkage. In addition to sialic acid, S may be modified sialic acid. For example, S may be sialic acid with the —OH group at the C4-position modified (e.g. by $C_1$-$C_4$ alkyl). Most preferably, S is unmodified sialic acid.

The monosaccharide compounds $(MS)_p$ and $(MS)_q$ may be any monosaccharide compound known in the art. For example, tetroses (e.g., erythrose and threose), pentoses (e.g., ribose, arabinose, xylose and lyxose) and hexoses (allose, altrose, glucose, mannose, gulose, idose, galactose and talose) are included. The monosaccharide compounds $(MS)_p$ and $(MS)_q$ may be preferably a pentose or a hexose, more preferably a hexose, further more preferably, glucose, mannose or galactose, and most preferably, glucose or galactose. The monosaccharide compounds $(MS)_p$ and $(MS)_q$ may be a D- or L-stereoisomer, most preferably a D-stereoisomer.

$(MS)_p$ and $(MS)_q$ may be the same or different monosaccharide compound. Preferably, they are different monosaccharide compounds.

According to a preferred embodiment of the present invention, $(MS)_p$ is galactose or glucose, and $(MS)_q$ is glucose or galactose. Most preferably, $(MS)_p$ is galactose and $(MS)_q$ is glucose. When $(MS)_p$ is galactose and $(MS)_q$ is glucose, the disaccharide compound lactose is obtained.

The monosaccharide compounds $(MS)_p$ and $(MS)_q$ may be modified or unmodified. For example, a monosaccharide compound with the —OH group bound to acetyl or N-acetyl may be used. Preferably, the monosaccharide compounds $(MS)_p$ and $(MS)_q$ are unmodified monosaccharide compounds.

The most preferred embodiment of the compound represented by General Formula I, which is used as the effective ingredient in the present invention, is sialyllactose. Sialyllactose, which is used as the effective ingredient in the present invention, is a compound formed by sequentially bound sialic acid, galactose and glucose.

Sialic acid may be bound to galactose in various manners, e.g. via α-2,3 or α-2,6 linkage. Sialic acid may be modified. For example, the —OH group at the C4-position of sialic acid may be modified (e.g. by $C_1$-$C_4$ alkyl).

The galactose and glucose in the sialyllactose may be D- or L-stereoisomers, most preferably D-stereoisomers. The galactose and glucose may be modified or unmodified. For example, the —OH group of the monosaccharide compound may be bound to acetyl or N-acetyl. Preferably, the galactose and glucose in the sialyllactose are unmodified monosaccharides.

According to a preferred embodiment of the present invention, the sialyllactose used in the present invention as the effective ingredient is α-NeuNAc-(2→3)-β-D-Gal-(1→4)-D-Glc or α-NeuNAc-(2→6)-β-D-Gal-(1→4)-D-Glc [NeuNAc: N-acetylneuraminyl, Gal: galactose, Glc: glucose]. α-NeuNAc-(2→3)-β-D-Gal-(1→4)-D-Glc is a substance found in GM3 ganglioside, and α-NeuNAc-(2→6)-β-D-Gal-(1→4)-D-Glc is its isomer.

More preferably, the sialyllactose used in the present invention as the effective ingredient is α-NeuNAc-(2→6)-β-D-Gal-(1→4)-D-Glc. As demonstrated in the examples below, α-NeuNAc-(2→6)-β-D-Gal-(1→4)-D-Glc is superior to α-NeuNAc-(2→3)-β-D-Gal-(1→4)-D-Glc in the effect of preventing or treating hyperlipidemia, fatty liver, cardiovascular disease or obesity.

In the composition of the present invention, in addition to the above-described compound itself, a pharmaceutically acceptable salt, hydrate or solvate thereof may be used as the effective ingredient.

The term "pharmaceutically acceptable salt" refers to a salt of the compound that produces the desired pharmacological effect, i.e. reduction of body weight and LDL-cholesterol. The salt is formed by using an inorganic acid (e.g., hydrochloride, hydrobromide and hydroiodide) or an organic acid (e.g., acetate, adipate, alginate, aspartate, benzoate, benzenesulfoate, p-toluenesulfoate, bisulfate, sulfamate, sulfate, naphtalate, butyrate, citrate, camphorate, camphorsulfonate, cyclopentaneptopionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate).

The term "pharmaceutically acceptable hydrate" refers to a hydrate of the compound that produces the desired pharmacological effect. The term "pharmaceutically acceptable solvate" refers to a solvate of the compound that produces the desired pharmacological effect. The hydrate and the solvate may also be prepared using the aforementioned acids.

The composition of the present invention comprising the compound represented by General Formula I or a pharmaceutically acceptable salt, hydrate or solvate thereof as an effective ingredient induces body weight loss, decrease of organ fat, decrease of total cholesterol level, increase of HDL-cholesterol level, decrease of LDL-cholesterol level and decrease of leptin level, thereby exhibiting prophylactic or therapeutic activity for hyperlipidemia, fatty liver, cardiovascular disease or obesity.

As used herein, the term "hyperlipidemia" refers to a condition of abnormally raised levels of lipids such as free cholesterol, cholesterol ester, phospholipid or triglyceride in the blood. Although hyperlipidemia itself does not usually results in symptoms, excessive lipids in the blood may adhere to the blood vessel wall and cause arteriosclerosis, thereby leading to coronary heart disease, cerebrovascular disease, peripheral arterial obstructive disease, or the like (E. Falk et al., *Circulation* 92, 657-671, 1995). In addition, fatty liver may be induced as the excessive lipids are accumulated in the liver tissue.

As used herein, the term "fatty liver" refers to a condition where the weight proportion of fat in the liver exceeds 5%. It may occur in those with excessive alcohol intake as well as those with excessive fat intake.

According to a preferred embodiment of the present invention, the cardiovascular disease that may be prevented or treated by the composition of the present invention is hypertension, heart failure, coronary artery disease, aneurysm, arteriosclerosis, atherosclerosis, myocardial infarction, embolism, stroke or thrombosis.

The composition of the present invention may be prepared into a pharmaceutical composition, a neutraceutical composition or a food composition.

According to a preferred embodiment of the present invention, the composition of the present invention is a pharmaceutical composition comprising (a) a pharmaceutically effective amount of the compound of the present invention represented by General Formula I; and (b) a pharmaceutically acceptable carrier.

As used herein, the term "pharmaceutically effective amount" refers to an amount sufficient to attain the effect or activity of the compound represented by General Formula I.

When the composition of the present invention is prepared into a pharmaceutical composition, the pharmaceutical composition of the present invention comprises a pharmaceutically acceptable carrier. The pharmaceutically acceptable carrier comprised in the pharmaceutical composition of the present invention is one commonly used in formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present invention may further comprise, in addition to aforesaid ingredients, a lubricant, a wetting agent, a sweetener, a flavor, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present invention may be administered orally or parenterally. In case of parenteral administration, it may be administered through intravenous injection, subcutaneous injection, intramuscular injection, intraperitoneal injection, transdermal administration, mucosal administration, ocular administration, or the like.

An adequate administration amount of the pharmaceutical composition of the present invention may vary depending on various factors including formulation method, administration method, age, weight, sex or disease condition of the patient, diet, administration time, administration route, elimination rate and response sensitivity. The pharmaceutical composition of the present invention may be preferably administered, for an adult, in an amount of 0.001-100 mg/kg (body weight) per day, more preferably 0.01-80 mg/kg (body weight), most preferably 0.1-60 mg/kg (body weight). Also, under the discretion of the physician or pharmacist, it may be administered once or several times per day.

The pharmaceutical or neutraceutical composition of the present invention may be prepared according to a method that may be easily carried out by those skilled in the art in single-dose forms or in multi-dose packages using a pharmaceutically acceptable carrier and/or excipient.

According to a preferred embodiment of the present invention, a formulation of the composition of the present invention may be solution, suspension, syrup, emulsion, liposome, extract, dust, powder, granule, tablet, sustained-release formulation or capsule, and may further comprise a dispersant or a stabilizer.

To describe more specifically according to administration route, a solid formulation for oral administration includes capsule, tablet, pill, dust and granule. In the solid formulation, the active compound may be mixed with one or more inert pharmaceutically acceptable excipient(s) or carrier(s) (e.g., sodium citrate or dicalcium phosphate) and/or a) filler or extender (e.g., starch, lactose, sucrose, glucose, mannitol and silicic acid), b) binder (e.g., carboxymethylcellulose, alginate, gelatin, polyvinylpyrrolidone, sucrose and gum arabic), c) humectant (e.g., glycerol), d) disintegrant (e.g., agar-agar, calcium carbonate, potato or tapioca starch, alginic acid, certain silicate and sodium carbonate), e) solution retarder (e.g., paraffin), f) absorption accelerator (e.g., quaternary ammonium compound), g) wetting agent (e.g., cetyl alcohol and glycerol monostearate), h) adsorbent (e.g., kaolin and bentonite) and i) lubricant (e.g., talc, calcium stearate, magnesium stearate, solid polyethylene glycol, sodium lauryl sulfate and mixture thereof). In the case of capsule, tablet and pill, the formulation may further comprise a buffering agent.

Further, in addition to an excipient such as lactose or milk sugar, polyethylene glycol or other polymer may be used in soft or hard gelatin capsule as a filler.

Solid administration forms such as tablet, sugar-coated tablet, capsule, pill and granule may be coated with enteric coating or other coat well known in the pharmaceutical field. These may optionally comprise an opacifier, and they may be formulated such that only the active ingredient is released at a particular site in the gastrointestinal tract in a sustained manner or preferentially. Also, if necessary, the active compound may be prepared into microcapsule together with the one or more excipient(s).

Liquid formulations for oral administration include pharmaceutically acceptable emulsion, solution, suspension, syrup and elixir. In addition to the active compound, the liquid formulation may comprise an inert diluent commonly used in the art such as, for example, water or other solvent, solubilizing agent and emulsifier (e.g., ethyl alcohol, isopropyl alcohol, ethyl carbonate, ethyl acetate, benzyl alcohol, benzyl benzoate, propylene glycol, 1,3-butylene glycol, dimethylformamide, oil (in particular, cottonseed, groundnut, corn, germ, olive, castor or sesame oil), glycerol, tetrahydrofuryl alcohol, polyethylene glycol and fatty acid ester of sorbitan, and mixtures thereof. Besides the inert diluent, the oral composition may also comprise an adjuvant such as a wetting agent, an emulsifier, a suspending agent, a sweetener, a flavor and a perfume.

A formulation for rectal or vaginal administration is preferably a suppository which can be prepared by mixing 윤 the compound of the present invention with suitable a non-irritating adjuvant or carrier (e.g., cocoa butter, polyethylene glycol or suppository wax) which is solid at ambient temperature but liquid at body temperature and therefore melts in the rectum or vaginal cavity and releases the active compound.

Formulations suitable for parenteral injection may include a physiologically acceptable sterile aqueous or oleaginous solution, dispersion, suspension or emulsion, and sterile powder which can be dissolved or dispersed in to prepare sterile injectable solution or dispersion. Examples of suitable aqueous or oleaginous carrier, diluent, solvent or vehicle include water, ethanol, polyol (propylene glycol, polyethylene glycol, glycerol, etc.), vegetable oil (olive oil), injectable organic ester (e.g., ethyl oleate), and adequate mixtures thereof.

Further, the composition of the present invention may comprise an adjuvant such as a preservative, a wetting agent, an emulsifier and a dispersant. Prevention of the action of microorganisms may be ensured by the inclusion of various antibacterial and antifungal agents (e.g., paraben, chlorobutanol, phenol, sorbic acid, etc.). It may be also desirable to include an isotonic agent such as sugar, sodium chloride, etc. In addition, prolonged absorption of the injectable formulation may be attained by the inclusion of an agent that delays absorption (e.g., aluminum monostearate and gelatin).

A suspension, in addition to the active compound, may comprise a suspending agent (e.g., ethoxylated isostearyl alcohol, polyoxyethylene sorbitol and sorbitan ester, microcrystalline cellulose, aluminum metahydroxide, bentonite, agar-agar and tragacanth, and mixtures thereof).

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

An injectable depot form is made by forming microencapsulated matrices of the drug in biodegradable polymers such as polylactide-polyglycolide. The rate of drug release may be determined depending on the ratio of the drug to polymer, and the nature of the particular polymer employed.

Examples of other biodegradable polymer include poly (orthoester) and poly(anhydride). A depot injectable formulation is also prepared by entrapping the drug in liposomes or microemulsions that are compatible with body tissue.

An injectable formulation may be sterilized by, for example, filtration through a bacteria-retaining filter, or by incorporating a sterilizing agent in the form of a sterile solid composition that can be dissolved or dispersed in sterile water or some other sterile injectable medium immediately before use.

According to a preferred embodiment of the present invention, the composition of the present invention is a composition for oral administration, and is in the form of a liposome or sustained-release formulation.

According to another preferred embodiment of the present invention, the composition of the present invention is a composition for parenteral administration, and is in the form of a liposome or sustained-release formulation.

The pharmaceutical composition of the present invention may be encapsulated in a liposome to provide stability for drug delivery. The liposome employed in the present invention may be prepared from a mixture of polyol, surfactant, phospholipid, fatty acid and water (Prescott, Ed., *Methods in Cell Biology*, (XIV), p. 33 et seq. (1976)).

The polyol used to prepare the liposome is not particularly limited, and preferably includes propylene glycol, dipropylene glycol, 1,3-butylene glycol, glycerin, methylpropanediol, isoprene glycol, pentylene glycol, erythritol, xylitol and sorbitol, most preferably propylene glycol.

The surfactant which can be used in the preparation of the liposome may be any surfactant known in the art, and examples thereof include an anionic surfactant, a cationic surfactant, an amphoteric surfactant and a non-ionic surfactant, preferably an anionic surfactant and a non-ionic surfactant. Specific examples of the anionic surfactant include alkyl acyl glutamate, alkyl phosphate, alkyl lactate, dialkyl phosphate and trialkyl phosphate. Specific examples of the non-ionic surfactant include alkoxylated alkyl ether, alkoxylated alkyl ester, alkyl polyglycoside, polyglyceryl ester and sugar ester. Most preferably, polysorbates are used as the non-ionic surfactant.

The phospholipid, another component used in the preparation of the liposome, is an amphoteric lipid, and includes natural phospholipids (e.g., egg lecithin, soybean lecithin or sphingomyelin) and synthetic phospholipids (e.g., dipalmitoylphosphatidylcholine or hydrogenated lecithin), preferably lecithin. More preferably, the lecithin is naturally occurring saturated or unsaturated lecithin extracted from soybean or egg yolk. In general, naturally occurring lecithin contains 23-95% of phosphatidylcholine and not more than 20% of phosphatidylethanolamine.

The fatty acid used in the preparation of the liposome is a higher fatty acid, preferably a saturated or unsaturated fatty acid having a $C_{12}$-$C_{22}$ alkyl chain, and includes, for example, lauric acid, myristic acid, palmitic acid, stearic acid, oleic acid and linoleic acid. The water used in the preparation of the liposome is, in general, deionized distilled water.

The liposome may be prepared by various methods known in the art. Most preferably, it is prepared by applying a mixture including the aforesaid components in a high-pressure homogenizer.

Thus prepared liposome system is advantageous in that it can maximize drug delivery by dissolving various hardly soluble materials and, at the same time, stabilizing unstable materials.

According to a preferred embodiment of the present invention, the composition of the present invention is administered using a skin roller. The skin roller is used to directly deliver a drug into the skin by loading the drug in a microneedle which penetrates the epidermis and dermis of the skin.

The pharmaceutical composition of the present invention may be prepared into a sustained-release formulation to continuously maintain an effective blood level of the effective ingredient, thereby reducing the number of medication and improving compliance.

The sustained-release formulation is prepared by adding, in addition to the effective ingredient of the present invention, a sustained-release carrier and other adjuvant. The sustained-release carrier used in the present invention may be various sustained-release carriers known in the art, preferably polyethylene oxide.

The other adjuvant used to prepare the sustained-release formulation may be a diluent carrier commonly in the pharmaceutical field. Examples of the diluent carrier used for this purpose include lactose, dextrin, starch, microcrystalline cellulose, calcium hydrogen phosphate, calcium carbonate, starch, silicon dioxide, etc. In addition, a glidant for improving flowability, such as zinc stearate or magnesium stearate, or other adjuvant that may be used in the pharmaceutical field may be included.

The pharmaceutical composition of the present invention may be used alone, but it may provide an effective anti-obesity effect when used in combination with other commonly used anti-obesity drug. Examples of the anti-obesity drug that may be used in combination with the pharmaceutical composition of the present invention include orlistat, sibutramine, metformin, exenatide, pramlintide, rimonabant, and mixtures thereof.

In case the composition of the present invention is prepared into a food composition (or neutraceutical composition), in addition to the compound represented by General Formula I as the effective ingredient, ingredients customarily used in food preparation, for example, protein, carbohydrate, fat, nutrient, seasoning and flavor, may be included. Examples of the carbohydrate include monosaccharides, e.g., glucose, fructose, etc.; disaccharides, e.g., maltose, sucrose, oligosaccharide, etc.; and polysaccharides, such as sugars, e.g., dextrin, cyclodextrin, etc. and sugar alcohols, e.g., xylitol, sorbitol, erythritol, etc. The flavor may be a natural flavor [thaumatin or stevia extract (e.g., rebaudioside A, glycyrrhizin, etc.]) or a synthetic flavor (saccharin, aspartame, etc.).

In case the food composition of the present invention is prepared into a drink, in addition to the compound of the present invention represented by General Formula I, for example, citric acid, liquid fructose, sucrose, glucose, acetic acid, malic acid, fruit juice, eucommia extract, jujube extract, licorice extract, etc. may be further included.

MODE FOR INVENTION

The examples and experiments will now be described. It will be apparent to those skilled in the art that the following examples and experiments are for illustrative purposes only and not intended to limit the scope of the present invention.

Example 1: Experiments with C56BL/6 Mouse

Decrease of Body Weight Increase of High-Fat Diet Mice 4 week-old C56BL/6 male mice were purchased from Dooyeul Biotech (Korea). Water was allowed freely and commercially available pellet feed (Dooyeul Biotech, Korea) was given for a week. The mice were grouped into six groups (six per each group) as follows: ND, normal diet group (normal group); HD, high-fat (60% fat) diet [purchased from Research Diets (New Brunswick, USA)] group (control group); and HD+SL (0.1 mg/kg), HD+SL (0.5 mg/kg), HD+SL (1.0 mg/kg) and HD+SL (5.0 mg/kg), high-fat diet groups treated with sialyllactose (SL, Sigma). Sialyllactose or PBS was administered every day by peritoneal injection. The mice were kept in cages for 50 days and sacrificed after fasting for 12 hours. Food intake and body weight change were measured every 7 days. 3'-Sialyllactose (3'-N-acetylneuraminyl-D-lactose, 3'-sialyl-D-lactose or α-NeuNAc-(2→3)-β-D-Gal-(1→4)-D-Glc) and 6'-sialyllactose (6'-N-acetylneuraminyl-lactose, 6'-sialyl-D-lactose or α-NeuNAc-(2→6)-β-D-Gal-(1→4)-D-Glc) were purchased from Sigma-Aldrich.

Figure 1B:
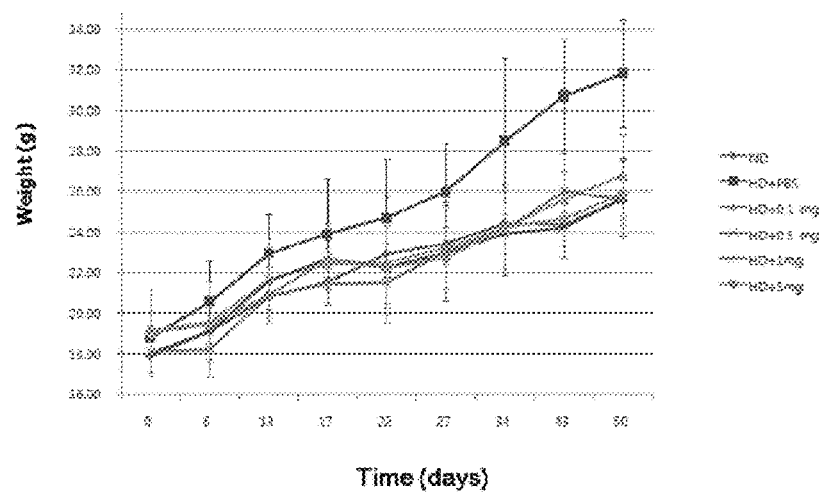
FIG. 1b is a graph showing the body weight change of high-fat diet C56BL/6 male mice [ND, HD and HD+6'-SL represent a normal diet group (normal group), a high-fat (60% fat) diet group (control group) and a high-fat diet group treated with 6'-sialyllactose (6'-SL), respectively.]

Body weight change of the high-fat diet C56BL/6 male mice is summarized in Tables 1a and 1b and FIGS. 1a and 1b.

TABLE 1a

| | HD + 3'-SL or 6'-SL (mg/kg) | | | |
|---|---|---|---|---|
| | ND | SL 0 | SL 0.1 | SL 0.5 |
| Initial weight (g) | 21.42 ± 1.11 | 22.00 ± 1.55 | 22.40 ± 1.58 | 22.90 ± 1.24 |
| | 18.40 ± 0.88(*) | 18.82 ± 0.54(*) | 19.00 ± 0.78(*) | 18.06 ± 0.99(*) |
| Final weight (g) | 25.82 ± 0.49 | 35.72 ± 5.50 | 31.34 ± 1.15 | 30.42 ± 0.51 |
| | 25.61 ± 0.98(*) | 31.84 ± 2.34(*) | 26.82 ± 0.92(*) | 25.74 ± 1.93(*) |
| Weight increase (g/50 day) | 4.41 ± 0.62 | 13.72 ± 4.65 | 8.94 ± 0.43 | 7.52 ± 0.74 |
| | 7.22 ± 1.43(*) | 13.02 ± 2.25(*) | 7.82 ± 1.44(*) | 7.68 ± 2.82(*) |
| Food intake | 2.00 ± 0.15 | 2.10 ± 0.11 | 2.31 ± 0.13 | 2.30 ± 0.17 |
| | 2.60 ± 0.13(*) | 2.74 ± 0.20(*) | 2.68 ± 0.13(*) | 2.56 ± 0.21(*) |

TABLE 1b

| | HD + 3'-SL or 6'-SL (mg/kg) | | |
|---|---|---|---|
| | ND | SL 1.0 | SL 5.0 |
| Initial weight (g) | 21.42 ± 1.11 | 23.40 ± 1.58 | 22.00 ± 1.22 |
| | 18.40 ± 0.88(*) | 17.63 ± 0.18(*) | 19.03 ± 0.21(*) |
| Final weight (g) | 25.82 ± 0.49 | 29.00 ± 0.82 | 28.68 ± 0.95 |
| | 25.61 ± 0.98(*) | 25.62 ± 1.33(*) | 25.92 ± 0.95(*) |
| Weight increase (g/50 day) | 4.41 ± 0.62 | 5.60 ± 0.77 | 6.68 ± 0.28 |
| | 7.22 ± 1.43(*) | 7.99 ± 1.15(*) | 6.88 ± 1.80(*) |
| Food intake | 2.00 ± 0.15 | 2.28 ± 0.13 | 2.27 ± 0.18 |
| | 2.60 ± 0.13(*) | 2.31 ± 0.21(*) | 2.62 ± 0.11(*) |

In Table 1, the data marked with (*) represent those for the mice treated with 6'-SL, and ND and HD represent normal diet group and high-fat diet group, respectively.

As seen in Tables 1a and 1b and FIGS. 1a and 1b, the mice treated with sialyllactose showed less increase of body weight. Especially, the mice treated with 6'-SL showed significant decrease in body weight increase.

Figure 2:
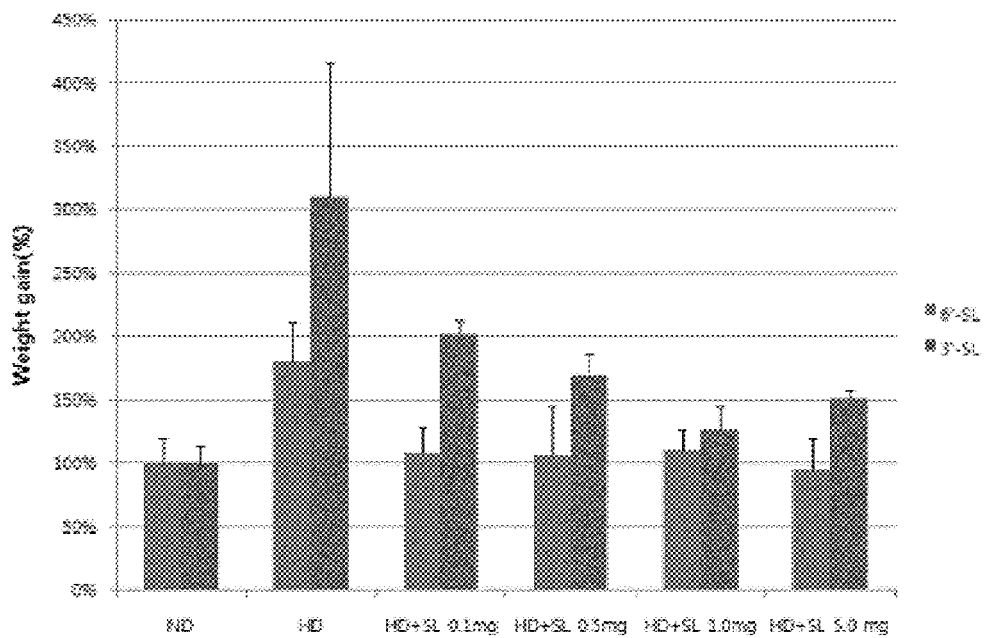
FIG. 2 is a graph comparing the body weight change of high-fat diet C56BL/6 male mice treated with 3'-SL and 6'-SL.
Figure 3A:
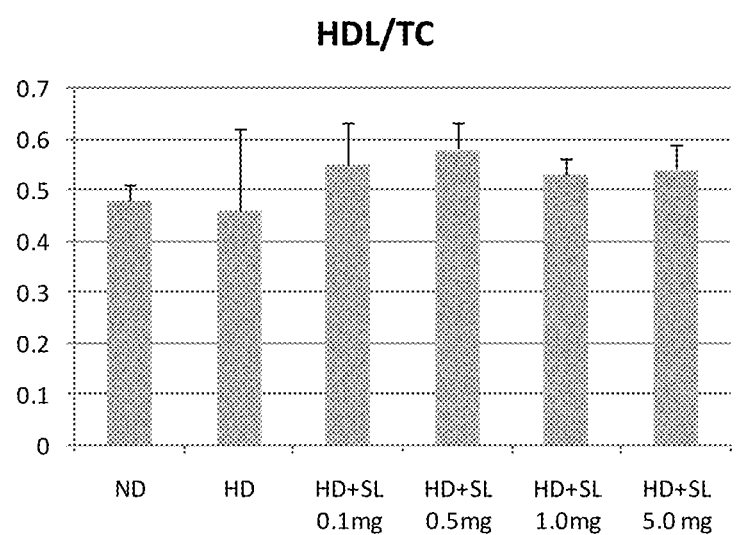
FIGS. 3a and 3d are graphs showing the change of lipid parameters in high-fat diet C56BL/6 male mice treated with 6'-SL.
Figure 3B:
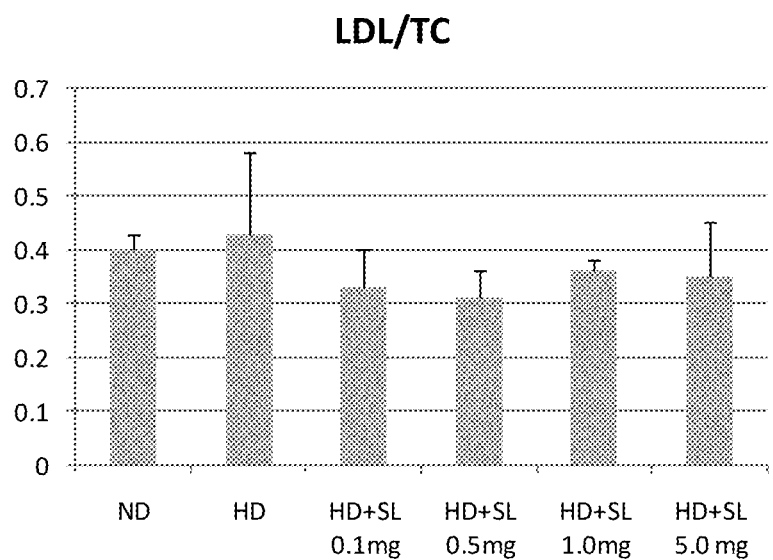
FIG. 3e is a graph showing the change of leptin level in high-fat diet C56BL/6 male mice treated with 6'-SL.
FIGS. 3f-3i are graphs showing the change of lipid parameters in high-fat diet C56BL/6 male mice treated with 3'-SL.
FIG. 3j is a graph showing the change of leptin level in high-fat diet C56BL/6 male mice treated with 3'-SL.
Figure 3C:
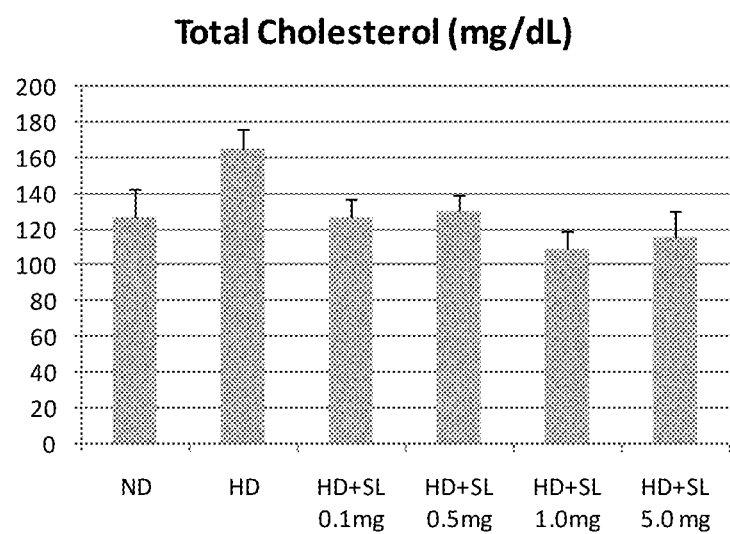
Figure 3D:
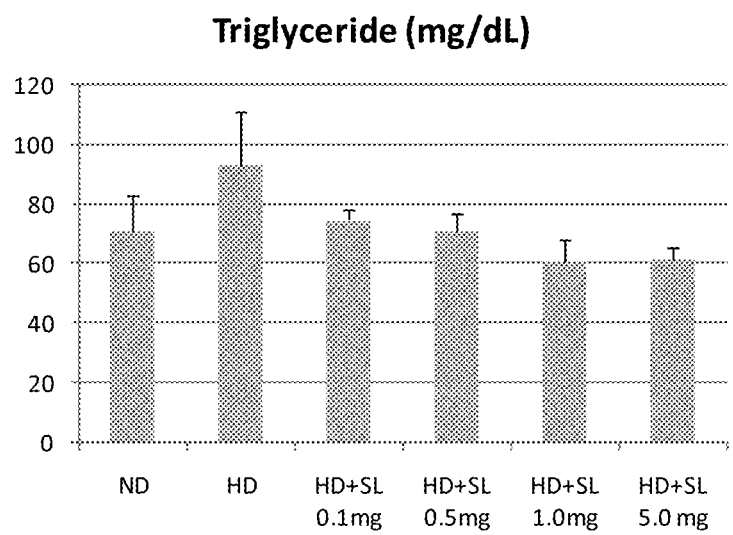
Figure 3E:
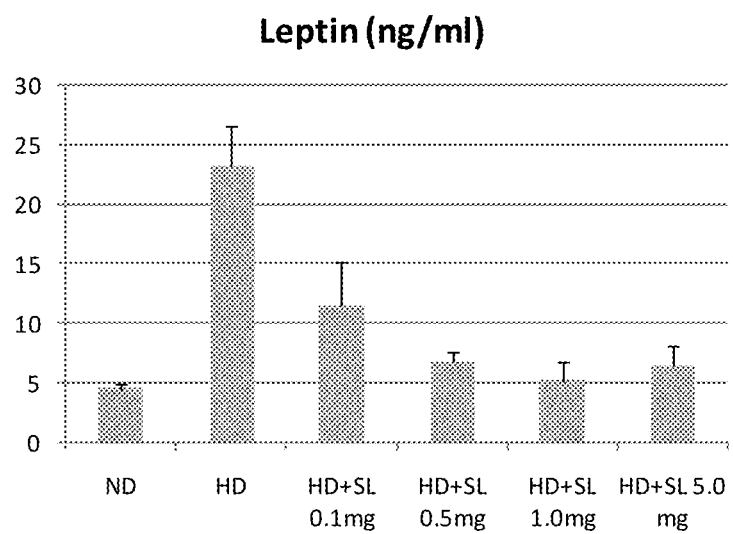
Figure 3F:
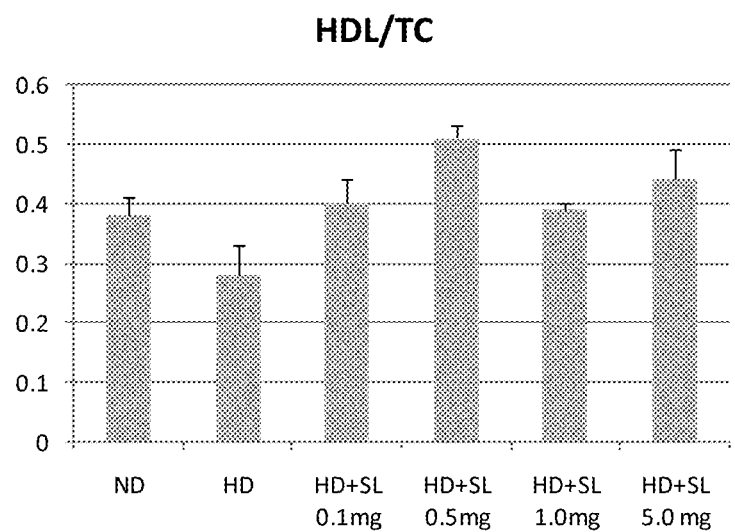
Figure 3G:
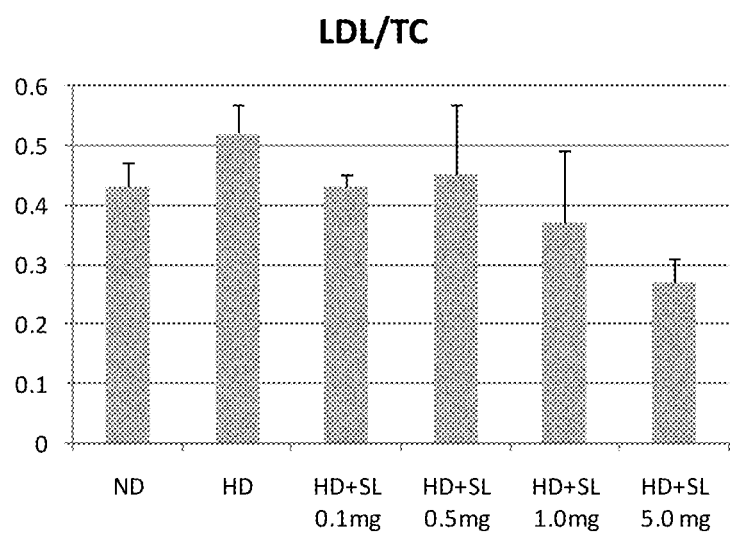
Figure 3H:
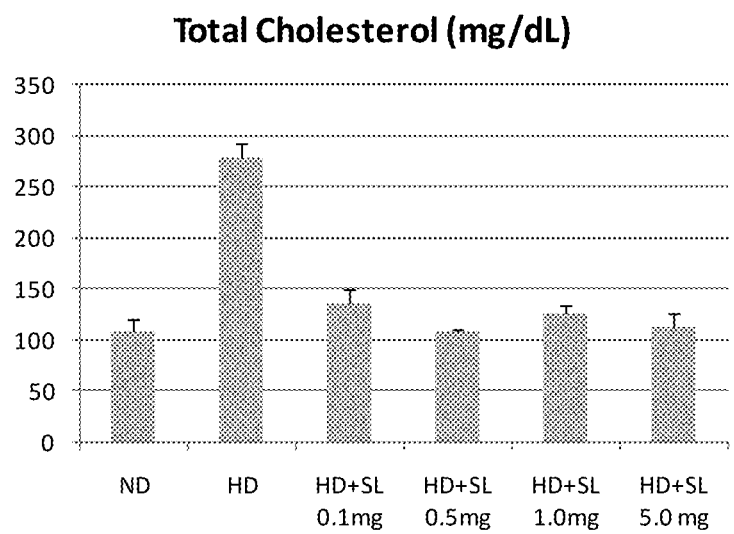
Figure 3I:
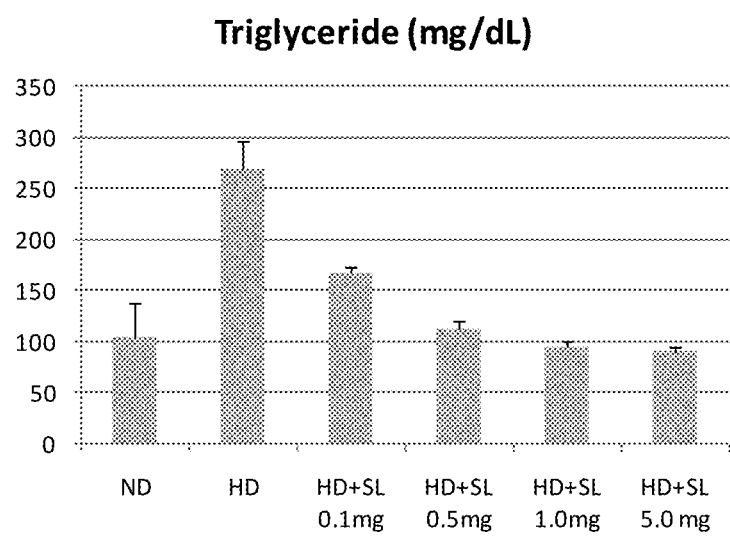
Figure 3J:
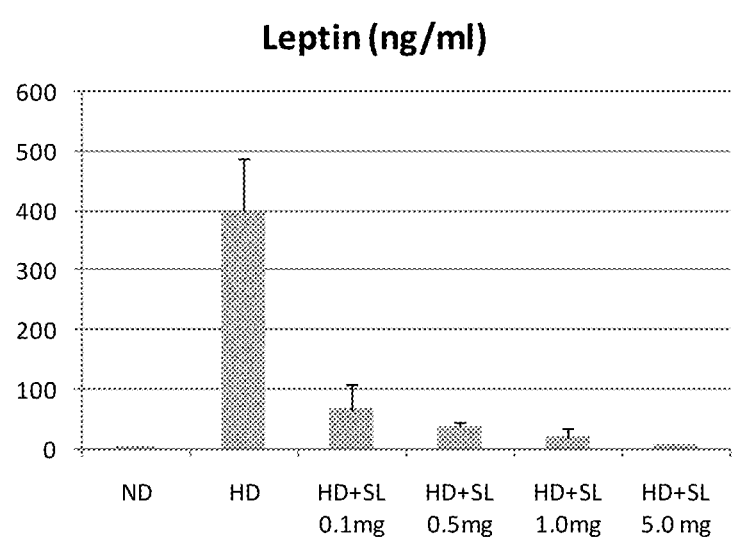

FIG. 2, which compares the body weight change of high-fat diet C56BL/6 male mice treated with 3'-SL and 6'-SL, clearly shows that 6'-SL is more effective in body weight loss than 3'-SL.

Body weight increase pattern of the mice to which 3'-SL or 6'-SL was peritoneally injected at a dose of 5 mg/kg was directly compared with the high-fat diet group and the normal control group (Table 2).

TABLE 2

| Comparison of body weight increase | 6'-SL | 3'-SL |
|---|---|---|
| HD vs. ND | 180.3% | 311.0% |
| SL vs. ND | −4.7% | 51.5% |

The mice which received the high-fat diet for 50 days showed body weight increase of over 300% compared to the normal diet mice. When SL was peritoneally injected at a dose of 5 mg/kg on top of the high-fat diet, 6'-SL resulted in body weight decrease by 4.7% and 3'-SL resulted in body weight increase by 51.5%. 6'-SL resulted in less body weight increase than the normal diet mice. Accordingly, it can be seen that 6'-SL provides better body weight loss effect than 3'-SL.

Effect on Lipid Level and Obesity in High-Fat Diet Mice

Blood was taken from the liver of the C56BL/6 male mice. The blood was coagulated, centrifuged for 15 minutes at 13,000 rpm, and kept at −20° C. until serum analysis. High-density lipoprotein (HDL)-cholesterol level was measured using an HDL kit (YD Diagnostics, Korea). Triglyceride (TG) was analyzed using a TG kit (YD Diagnostics) based on enzymologic method. Total cholesterol was analyzed using a cholesterol E kit (YD Diagnostics). Low-density lipoprotein (LDL)-cholesterol level was calculated from triglyceride level, total cholesterol level and HDL-cholesterol level according to Equation 1:

$$\text{LDL-cholesterol} = \text{total cholesterol} - \{(\text{HDL-cholesterol} - \text{triglyceride}) + 5\} \qquad \text{Equation 1}$$

Leptin level was measured using a mouse leptin ELISA kit (Millipore) and a rat leptin ELISA kit (Millipore).

Test result is summarized in Tables 3a and 3b and FIGS. 3a-3j.

TABLE 3a

| Lipid (mg/dL) | ND | HD + 3'-SL or 6'-SL (mg/kg) | | |
|---|---|---|---|---|
| | | SL 0 | SL 0.1 | SL 0.5 |
| HDL-cholesterol | 41.03 ± 4.83 | 78.50 ± 12.77 | 53.27 ± 5.08 | 55.74 ± 3.18 |
| | 61.93 ± 10.53(*) | 75.11 ± 20.74(*) | 70.71 ± 14.15(*) | 76.33 ± 10.53(*) |
| LDL-cholesterol | 46.32 ± 6.77 | 146.28 ± 18.47 | 58.16 ± 3.74 | 48.43 ± 13.91 |
| | 50.97 ± 3.53(*) | 70.90 ± 21.38(*) | 41.07 ± 6.34(*) | 40.00 ± 4.25(*) |
| Total cholesterol (TC) | 108.08 ± 12.15 | 278.68 ± 13.28 | 135.05 ± 13.58 | 108.25 ± 3.06 |
| | 127.12 ± 15.0(*) | 164.61 ± 11.3(*) | 126.68 ± 10.7(*) | 130.54 ± 8.10(*) |
| HDL/TC | 0.38 ± 0.03 | 0.28 ± 0.05 | 0.40 ± 0.04 | 0.51 ± 0.02 |
| | 0.48 ± 0.03(*) | 0.46 ± 0.16(*) | 0.55 ± 0.08(*) | 0.58 ± 0.05(*) |
| LDL/TC | 0.43 ± 0.04 | 0.52 ± 0.05 | 0.43 ± 0.02 | 0.45 ± 0.12 |
| | 0.40 ± 0.03(*) | 0.43 ± 0.15(*) | 0.33 ± 0.07(*) | 0.31 ± 0.05(*) |
| Triglyceride | 103.68 ± 35.04 | 269.55 ± 26.97 | 166.78 ± 6.60 | 112.99 ± 8.16 |
| | 71.06 ± 11.81(*) | 92.98 ± 17.87(*) | 74.48 ± 3.77(*) | 71.05 ± 5.88(*) |
| Leptin (ng/mL) | 4.93 ± 0.51 | 399.36 ± 89.54 | 66.59 ± 43.57 | 38.73 ± 5.58 |
| | 4.47 ± 0.48(*) | 23.19 ± 3.43(*) | 11.50 ± 3.72(*) | 6.71 ± 0.93(*) |

TABLE 3b

| Lipid (mg/dL) | ND | HD + 3'-SL or 6'-SL (mg/kg) | |
|---|---|---|---|
| | | SL 1.0 | SL 5.0 |
| HDL-cholesterol | 41.03 ± 4.83 | 49.29 ± 3.40 | 48.97 ± 1.62 |
| | 61.93 ± 10.53(*) | 57.44 ± 0.87(*) | 62.73 ± 8.58(*) |
| LDL-cholesterol | 46.32 ± 6.77 | 46.03 ± 13.79 | 29.91 ± 2.69 |
| | 50.97 ± 3.53(*) | 39.56 ± 8.53(*) | 40.36 ± 2.69(*) |
| Total cholesterol (TC) | 108.08 ± 12.15 | 126.30 ± 7.75 | 112.97 ± 12.54 |
| | 104.87 ± 5.26(*) | 109.14 ± 9.86 (*) | 115.36 ± 14.9(*) |
| HDL/TC | 0.38 ± 0.03 | 0.39 ± 0.01 | 0.44 ± 0.05 |
| | 0.48 ± 0.03(*) | 0.53 ± 0.03(*) | 0.54 ± 0.05(*) |
| LDL/TC | 0.43 ± 0.04 | 0.37 ± 0.12 | 0.27 ± 0.04 |
| | 0.40 ± 0.03(*) | 0.36 ± 0.02(*) | 0.35 ± 0.10(*) |
| Triglyceride | 103.68 ± 35.04 | 94.28 ± 5.66 | 89.78 ± 4.31 |
| | 71.06 ± 11.81(*) | 60.69 ± 7.69(*) | 61.34 ± 3.84(*) |
| Leptin (ng/mL) | 4.93 ± 0.51 | 19.29 ± 14.24 | 6.64 ± 2.93 |
| | 4.47 ± 0.48(*) | 5.15 ± 1.61(*) | 6.47 ± 1.64(*) |

In Table 3, the data marked with (*) represent those for the mice treated with 6'-SL, and ND and HD represent normal diet group and high-fat diet group, respectively.

As seen in Tables 3a and 3b and FIGS. 3a-3j, the test groups treated with SL showed markedly decreased LDL-cholesterol, total cholesterol and triglyceride levels as compared to the high-fat diet group.

Decreased leptin indicates that the number of adipocytes decreases, which means that atherosclerosis may be prevented. The test groups treated with SL showed markedly decreased leptin level as compared to the high-fat diet group.

And, 6'-SL showed much better effect of reducing LDL-cholesterol, total cholesterol, triglyceride and leptin levels than 3'-SL.

To conclude, it can be seen that SL, in particular 6'-SL, reduces LDL-cholesterol, total cholesterol, triglyceride and leptin levels, and is capable of improving obesity, hyperlipidemia or cardiovascular disease.

Improvement of Fatty Liver in High-Fat Diet Mice

In order to investigate 3'-SL's effect of improving fatty liver, high-fat diet C56BL/6 male mice were dissected and the liver and other organs were observed.

Figure 4:
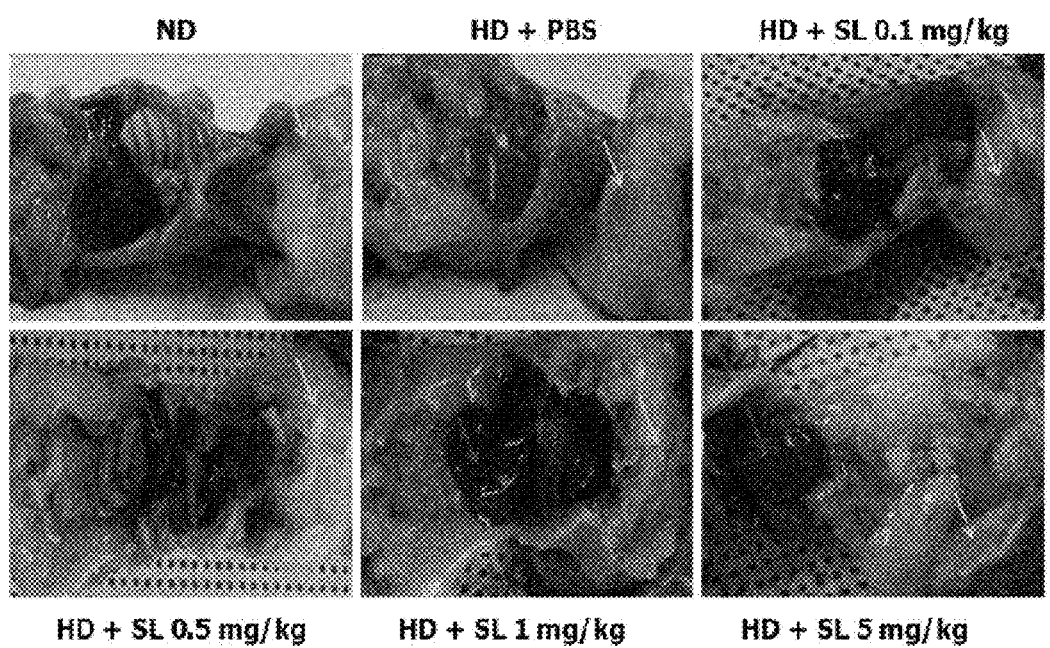
FIG. 4 shows photographs showing the effect of the administration of 3'-SL to high-fat diet C56BL/6 male mice on fatty liver.

As seen in FIG. 4, the high-fat diet mice showed fatty liver, and fats were accumulated not only in the liver but also in other organs. However, the mice to which 3'-SL was peritoneally administered had the liver almost the same as that of the normal diet (ND) mouse, and fat accumulation was not observed in the liver or other organs.

Effect on Subcutaneous Fat and Peritoneal Fat

Figure 5A:
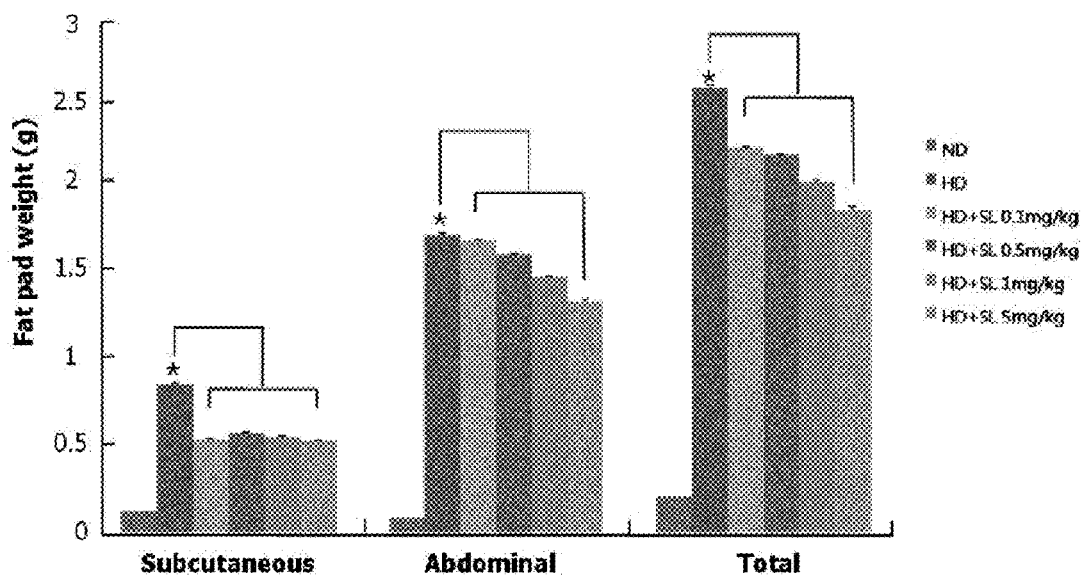
FIG. 5a is a graph showing the effect of the administration of 3'-SL to high-fat diet C56BL/6 male mice on subcutaneous or peritoneal fat.
Figure 5B:
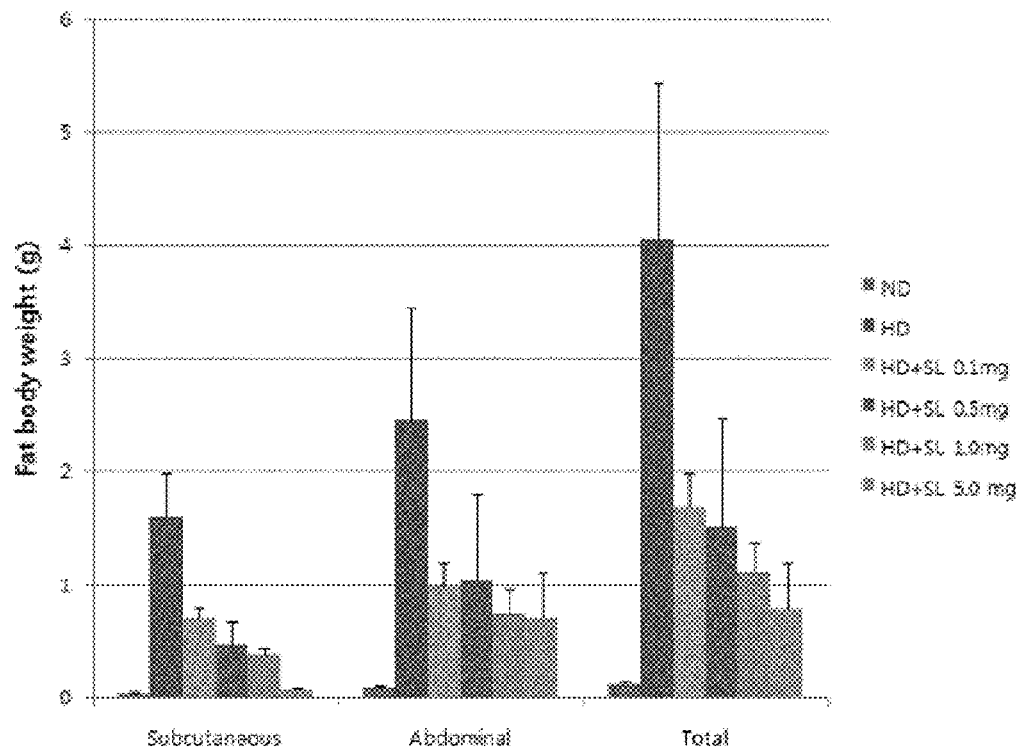
FIG. 5b is a graph showing the effect of the administration of 6'-SL to high-fat diet C56BL/6 male mice on subcutaneous or peritoneal fat.

As described above, 4 week-old C56BL/6 male mice were given high-fat diet and treated with SL for 6 weeks. Then, subcutaneous fat and peritoneal fat were isolated from the mice and weighed. As seen in FIGS. 5a and 5b, the mice to which SL was peritoneally administered showed dose-dependent decrease of subcutaneous fat and peritoneal fat.

Example 2: Experiments with SD Rats

Decrease of Body Weight Increase of High-Fat Diet Rats 4 week-old Sprague-Dawley (SD) rats were purchased from Dooyeul Biotech (Korea). Water was allowed freely and commercially available pellet feed (Dooyeul Biotech, Korea) was given for a week. The rats were grouped into four groups (six per each group) as follows: ND, normal diet group (normal group); HD, high-fat (60% fat) diet [purchased from Research Diets (New Brunswick, USA)] group (control group); and HD+SL (1 mg/kg) and HD+SL (5 mg/kg), high-fat diet groups treated with SL (Sigma). 3'-SL or deionized water (DW) was orally administered every day. The mice were kept in cages for 7 weeks and sacrificed after fasting for 12 hours. Food intake and body weight change were measured every 5 days.

Figure 6A:
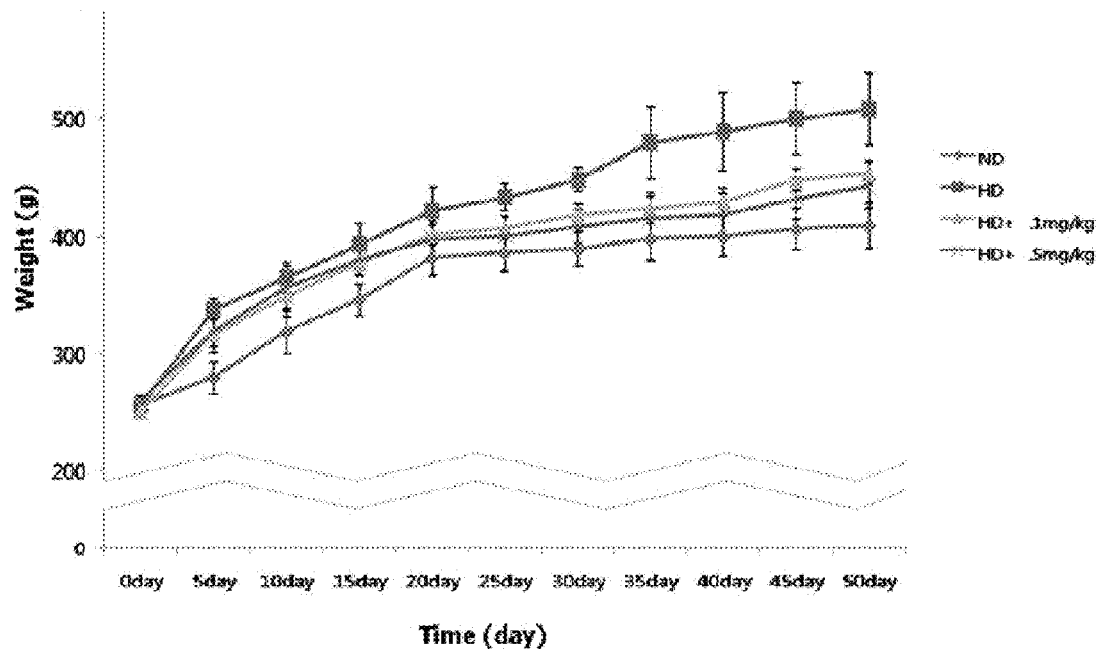
FIGS. 6a and 6b are graphs showing the body weight change of high-fat diet SD rats [3'-SL was administered at a dose of 1 mg/kg or 5 mg/kg]
Figure 6B:
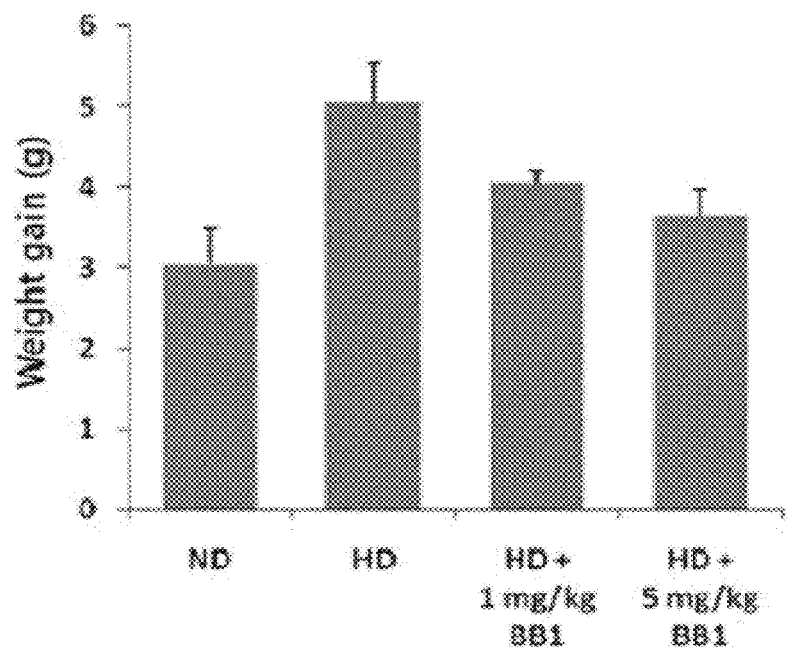

Body weight change of the high-fat diet SD rats is summarized in Table 4 and FIGS. 6a and 6b.

TABLE 4

| | ND | HD + SL (mg/kg) | | |
|---|---|---|---|---|
| | | SL 0 | SL 1.0 | SL 5.0 |
| Initial weight (g) | 256.60 ± 9.18 | 256.00 ± 5.56 | 251.60 ± 2.40 | 260.40 ± 3.71 |
| Final weight (g) | 409.00 ± 31.54 | 508.33 ± 30.74 | 454.17 ± 10.37 | 443.33 ± 19.56 |
| Weight increase (g/day) | 3.05 ± 0.45 | 5.05 ± 0.50 | 4.05 ± 0.16 | 3.66 ± 0.32 |
| Food intake (g/day) | 23.86 ± 1.25 | 23.20 ± 1.08 | 23.46 ± 0.82 | 24.08 ± 1.22 |
| Water intake (mL/day) | 59.91 ± 2.66 | 54.73 ± 2.80 | 54.27 ± 2.53 | 55.36 ± 3.32 |

In Table 4, SL represents 3'-sialyllactose, and ND and HD represent normal diet group and high-fat group, respectively.

As seen in Table 4 and FIGS. 6a and 6b, the rats to which sialyllactose was administered showed decreased body weight increase in a dose-dependent manner.

Effect on Subcutaneous Fat, Perirenal Fat and Retroperitoneal Fat

As described above, 4 week-old SD rats were treated with high-fat diet and 3'-SL for 6 weeks. Then, subcutaneous fat, perirenal fat and retroperitoneal fat were isolated from the rats and weighed.

Figure 7:
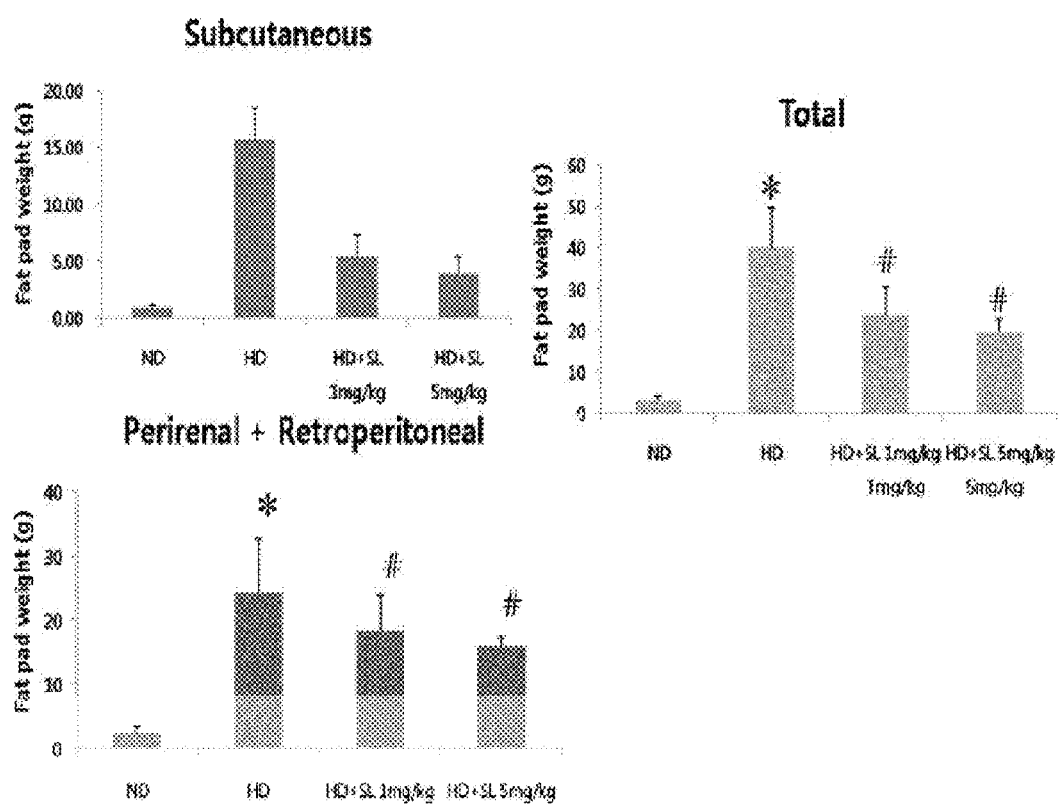
FIG. 7 is a graph showing the effect of the administration of 3'-SL to high-fat diet SD rats on subcutaneous, perirenal and retroperitoneal fat.

As seen in FIG. 7, the rats to which 3'-SL was orally administered showed decreased subcutaneous fat, perirenal fat and retroperitoneal fat in a dose-dependent manner. The total fat weight also decreased.

Serum Lipid Levels

Blood was taken from the liver of the SD rats, and lipid levels were analyzed in the same manner as the experiment with the C57BL/6 male mice.

TABLE 5

|  | HD | HD + SL |
|---|---|---|
| HDL-cholesterol | 64.59 ± 2.32 | 88.73 ± 1.32 |
| LDL-cholesterol | 77.30 ± 2.21 | 57.91 ± 1.39 |
| Total cholesterol | 211.32 ± 11.94 | 171.44 ± 12.8 |
| Triglyceride | 189.14 ± 3.24 | 149.00 ± 3.86 |
| HDL/total cholesterol | 0.31 ± 0.03 | 0.52 ± 0.04 |
| LDL/total cholesterol | 0.36 ± 0.02 | 0.34 ± 0.03 |

As seen in Table 5, the test group treated with 3'-SL (HD+SL 1 mg/kg) shoed higher HDL-cholesterol level and lower LDL-cholesterol, total cholesterol and triglyceride levels as compared to the control group. Accordingly, it can be seen that 3'-SL increases blood HDL-cholesterol level and reduces LDL-cholesterol level, and, therefore, has the effect of improving hyperlipidemia or cardiovascular disease.

Effect of Improving Fatty Liver in Obesity Model

In order to investigate 3'-SL's effect of improving fatty liver, high-fat diet SD rats were dissected and the liver and other organs were observed.

Figure 8A:
FIGS. 8a and 8b are photographs showing the effect of the administration of 3'-SL to high-fat diet SD rats on fatty liver [Left arrow indicates liver and right arrow indicates other organ.].
Figure 8B:
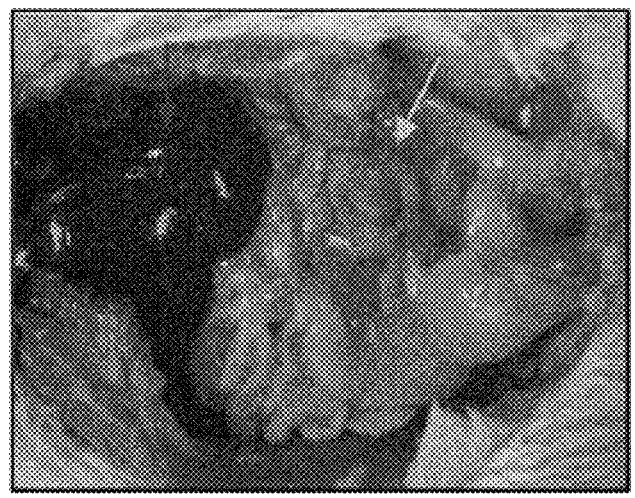

FIG. 8a shows the result for the high-fat diet group (control group), and FIG. 8b shows the result for the high-fat diet group. As seen in FIG. 8a, the high-fat diet rats showed fatty liver, and fats were accumulated not only in the liver but also in other organs. However, in the liver and other organs of the rats to which 3'-SL was orally administered, fat accumulation reduced markedly.

As described in detail above, the present invention provides a composition for prophylaxis or treatment of hyperlipidemia, fatty liver, cardiovascular disease or obesity comprising the compound represented by General Formula I as an effective ingredient. The compound used as the effective ingredient of the present invention induces body weight loss, decrease of organ fat, decrease of total cholesterol level, increase of HDL-cholesterol level, decrease of LDL-cholesterol level and decrease of leptin, and thereby provides prophylactic or therapeutic activity for hyperlipidemia, fatty liver, cardiovascular disease or obesity. Also, because it has no cytotoxicity or skin side effect, the composition of the present invention may be safely used as a pharmaceutical composition, a neutraceutical composition or a food composition.

While the present invention has been described with respect to the specific embodiments, it will be apparent to those skilled in the art that various changes and modifications may be made without departing from the spirit and scope of the invention as defined in the following claims.

The invention claimed is:

1. A method for treatment of a human having or at risk of developing hyperlipidemia, fatty liver, atherosclerosis, or obesity comprising administering a composition comprising sialyllactose, which is a-NeuNAc-(2→3)-β-D-Gal-(1→4)-D-Glc or a-NeuNAc-(2-6)-β-D-Gal-(1→4)-D-Glc, or a pharmaceutically acceptable salt thereof, in an amount that is effective for said treatment to a human in need of such treatment, wherein the effective amount is in the range of 0.001-100 mg/kg of the subject's body weight per day.

2. The method according to claim 1, wherein the sialyllactose is α-NeuNAc-(2→6)-β-D-Gal-(1→4)-D-Glc or a pharmaceutically acceptable salt thereof.

3. The method according to claim 1, wherein the composition is a pharmaceutical composition.

4. The method according to claim 1, wherein the composition is a formulation selected from a group consisting of solution, suspension, syrup, emulsion, liposome, dust, powder, granule, tablet, sustained-release formulation and capsule.

5. The method according to claim 4, wherein the composition is a composition for oral administration and is liposome or sustained-release formulation.

6. The method according to claim 4, wherein the composition is a composition for parenteral administration and is liposome or sustained-release formulation.

7. The method according to claim 1, wherein the composition is administered using a skin roller.

8. The method according to claim 1, wherein said method is for treatment of a human having or at risk of developing hyperlipidemia, fatty liver, or atherosclerosis.

9. The method according to claim 8, wherein said human has hyperlipidemia, fatty liver, or atherosclerosis.

10. The method of claim 1, wherein the sialyllactose is chemically or enzymatically synthesized, or is produced by metabolic engineering.

11. A method for alleviating symptoms of hyperlipidemia, fatty liver, atherosclerosis, or obesity in a subject in need thereof, comprising administering to the subject a composition comprising sialyllactose, which is a-NeuNAc-(2→3)-β-D-Gal-(1→4)-D-Glc or a-NeuNAc-(2→6)-β-D-Gal-(1→4)-D-Glc, or a pharmaceutically acceptable salt thereof, in an amount that is effective for said alleviating of said symptoms in the subject wherein the effective amount is in the range of 0.001-100 mg/kg of the subject's body weight per day.

12. The method of claim 1, wherein the human has or is at risk of developing hyperlipidemia.

13. The method of claim 1, wherein the human has or is at risk of developing fatty liver.

14. The method of claim 1, wherein the human has or is at risk of developing atherosclerosis.

15. The method of claim 1, wherein said composition consists of said sialyllactose, which is α-NeuNAc-(2→3)-β-D-Gal-(1→4)-D-Glc or α-NeuNAc-(2→6)-β-D-Gal-(1→4)-D-Glc, or a pharmaceutically acceptable salt thereof, and one or more pharmaceutically acceptable excipients.

16. The method of claim 1, wherein the composition is in the form of a nutritional beverage.

17. The method of claim 1, wherein the composition is in the form of a food product.

18. The method of claim 11, wherein the sialyllactose is chemically or enzymatically synthesized, or produced by metabolic engineering.

19. A method for treatment of a human having or at risk of developing hyperlipidemia, fatty liver, or atherosclerosis, or for alleviating a symptom thereof, comprising administering sialyllactose, which is a-NeuNAc-(2→3)-β-D-Gal-(1→4)-D-Glc or a-NeuNAc-(2→6)-β-D-Gal-(1→4)-D-Glc, or a pharmaceutically acceptable salt thereof, to a human in need of such treatment wherein the effective amount is in the range of 0.001-100 mg/kg of the subject's body weight per day.

* * * * *